United States Patent
O'Lenick, Jr. et al.

(10) Patent No.: US 6,180,668 B1
(45) Date of Patent: Jan. 30, 2001

(54) RECONSTITUTED MEADOWFOAM OIL IN PERSONAL CARE APPLICATIONS

(75) Inventors: Anthony J. O'Lenick, Jr., Dacula, GA (US); Alan Wohlman, Northbrook, IL (US)

(73) Assignee: Fan Tech LTD, Chicago, IL (US)

( * ) Notice: Under 35 U.S.C. 154(b), the term of this patent shall be extended for 0 days.

(21) Appl. No.: 09/330,207

(22) Filed: Jun. 11, 1999

Related U.S. Application Data

(63) Continuation-in-part of application No. 09/128,271, filed on Aug. 3, 1998, now Pat. No. 6,013,818, which is a continuation-in-part of application No. 08/993,604, filed on Dec. 18, 1997, now abandoned.

(51) Int. Cl.$^7$ ............................. A01N 37/02; A01N 37/06

(52) U.S. Cl. ............................................. 514/547; 514/873
(58) Field of Search ...................................... 514/547, 873

(56) References Cited

U.S. PATENT DOCUMENTS 5,454,965    10/1995    Shanahan .............................. 525/27

*Primary Examiner*—Deborah D. Carr

(57) ABSTRACT

The present invention relates to a series of "reconstituted meadowfoam oils", used on skin for moisturizing and emmolient applications. The term reconstituted as used hereon refers to a process in which meadowfoam oil and one or more oils of natural origin are transesterified under conditions of high temperature and catalyst to make a "reconstituted product" having an altered alkyl distribution and consequently altered chemical and physical properties.

14 Claims, No Drawings

RECONSTITUTED MEADOWFOAM OIL IN PERSONAL CARE APPLICATIONS

RELATED APPLICATION

This application is a continuation in part of U.S. patent application Ser. No. 09/128,271, filed Aug. 3, 1998, now U.S. Pat. No. 6,013,818, which is in turn a continuation in part of U.S. application Ser. No. 08/993,604 filed Dec. 18, 1997, now abandoned.

FIELD OF THE INVENTION

The present invention relates to the cosmetic use of a series of oils that have been "reconstituted". The term reconstituted as used hereon refers to a process in which two or more waxes or oils of natural origin are transesterified under conditions of high temperature and catalyst to make a "reconstituted product" having an altered alkyl distribution and consequently altered chemical and physical properties. The oils useful in the preparation of the compounds of the present invention include meadowfoam oil and another oil selected from the group consisting of soybean oil, corn oil, sunflower oil, safflower oil, olive oil and cottonseed oil. The reconstituted oil made from meadowfoam oil has unique feel on the skin without having an undesirable odor.

BACKGROUND

Natural waxes and oils fall into two distinct classes, based upon their chemistry. The first class is made up on the triglycerides and are generally referred to as oils. They are triesters of glycerin, hence the name triglycerides. The structure of the triglyceride is:

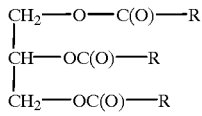

Naturally occurring triglycerides are natural products derived from plant species and have a species specific carbon distribution in the "R" portion. For example Soybean oil has a naturally occurring "R" 29% oleic $C_{17}H_{33}$ (oleic), and 54% linoleic $C_{17}H_{31}$ (linoleic). Soybean oil is a low viscosity oil that is not good for dispersing pigments.

The use of meadowfoam oil, in the preparation of reconstituted oils results in unique, unexpected oxidative stability rendered to the reconstituted oil. Specifically, the reconstituted oils containing minor amounts of meadowfoam oil have unexpected improvements in their oxidative stability.

The unique structure of the meadowfoam results in this oxidative stability heretofore unattainable. The fatty distribution of the oil ranges from 20 to 22 carbons and has unsaturation in specific locations. The oil contains 97% by weight higher unsaturated alkyl groups. Typically, meadowfoam oil contains 60–65% of a twenty carbon mono-carboxy acid having one unsaturation between carbon 5 and 6. Additionally, it contains 12–20% of a twenty two carbon mono-carboxy acid having one unsaturation between either carbon 5 and 6, or carbon 13 and 14 and 15–28% of a twenty two carbon mono-carboxy acid having one unsaturation between both carbon 5 and 6, or carbon 13 and 14. The combination of the fact that there are 20 to 22 carbon atoms in the group leads to lack of volatility, the presence of unsaturation leads to liquidity and the fact that the di-unsaturated moieties are not conjugated leads to outstanding oxidative stability.

Meadowfoam oil is a triglyceride that conforms to the following structure:

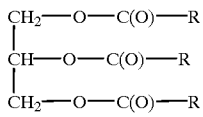

Wherein R is:
  60–65% by weight —$(CH_2)_3$-CH=CH-$(CH_2)_{13}$-$CH_3$
  12–20% by weight a mixture of —$(CH_2)_3$-CH=CH-$(CH_2)_{15}$-$CH_3$ and —$(CH_2)_{11}$-CH=CH-$(CH_2)_7$-$CH_3$ and
  and
  15–28% by weight
    —$(CH_2)_3$-CH=CH-$(CH_2)_6$-CH=CH-$(CH_2)_6$-$CH_3$.

The process of the current invention will allow for the synthesis of a reconstituted oil having a "mixed" carbon distribution and very desirable properties that can be customized for particular applications.

Another example of where reconstitution improves properties is mitigation of drying properties in so called drying oils. These oils have a high iodine value, generally over 175. These oils homo-polymerize to make films and generate heat. The heat is not properly dissipated can cause spontaneous combustion. By reacting a high iodine value oil with a lower iodine value oil we can lower the heat generated and the hardness of the film that forms.

It must be understood that these are not blends of oils. For example, if one blends meadowfoam oil and jojoba oil, the resultant mixture is s cloudy mass, that rapidly separates on standing. The process of the present invention makes the compounds react and remain clear and homogeneous. Not only that, the range of meadowfoam to Jojoba can be altered widely to change functional properties.

Beeswax separates from soybean oil, but when reacted according to the process of our invention, remains clear and results in an altered melting point and hardness of the resulting wax. The process allows for very wide variation and preparation of materials heretofore unattainable.

The term "wax" refers to a series of esters. Unlike triglycerides that are tri-esters of glycerin, these products are monoesters having alkyl distributions on both sides of the ester. A typical ester is beeswax. Beeswax conforms to the following structure:

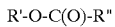

Botanists attempt to alter the distribution of the "R" group using genetic engineering and plant selection processes for both waxes and esters. This is a difficult, expensive and time-consuming process that allows for only marginal modification of the "R" group in natural oils. We have discovered that by using a process called "Reconstitution of the waxes or oils" we are able to prepare compounds that can be made to vary far more radically in "R' composition and consequently have new unique and controllable properties, heretofore unattainable using genetic manipulation and plant selection. The present invention to provides a series of products that are produced by this process for use in applications where the altered properties can be used. For example the modification of the melting point of beeswax by reconstituting it with soybean oil results in an ability to custom tailor melting points of the resulting wax for use in lipsticks, where the ability to have a melting point near body temperature is important. Another example of an application is pigment processing. Meadowfoam oil is commonly used as a solvent for milling pigment. The high viscosity of meadowfoam oil can be a problem however. By reconstituting meadowfoam oil and coconut oil the viscosity can be made to a desired value and the pigment dispersing ability and viscosity specifically controlled. Attempts to control these properties by genetic engineering have not been successful. We can simply make more and different variations of reconstituted products than can be bio-engineered.

THE INVENTION

Objective of the Invention

It is the objective of the present invention to provide unique and heretofore unknown reconstituted oils and waxes having unique oxidative stability, when applied to skin. It is another objective of the present invention to provide a series of products that are produced by this process for use cosmetic skin care applications where the malodor of other oils is objectionable. Other objectives will become clear reading the disclosure.

Summary of the Invention

Detailed Description of the Invention

There are three different combination of raw materials that can be used to practice the current invention. They are:

1. Two or more different triglycerides—A process for reconstituting triglycerides which comprises reacting two or more triglycerides having different "R" functionalities with each other to produce a reconstituted triglyceride. Typical of this reaction is the reconstitution of 0.33 moles of soybean oil and 0.67 moles of meadowfoam oil to produce a new reconstituted oil.

The reaction is as follows:

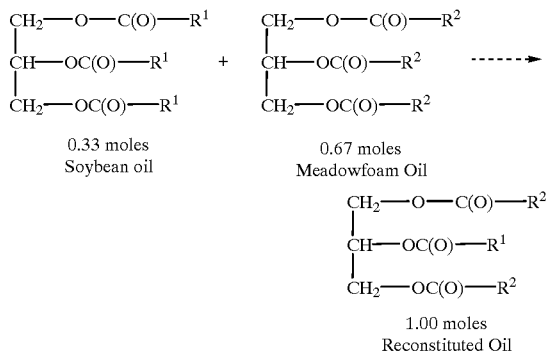

2. Two or more different waxes—A process for reconstituting waxes which comprises reacting two or more waxes having different "R" functionalities with each other to produce a reconstituted wax. Typical of this reaction is the reconstitution of 1.0 moles of beeswax and 1.0 moles of Jojoba to produce a new reconstituted wax.

The reaction is as follows:

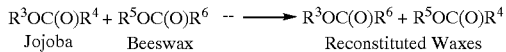

3. One or more waxes and one or more triglyceride—A process for reconstituting triglycerides and waxes which comprises: reacting one or more triglyceride and one or more waxes with each other to produce a reconstituted wax and reconstituted triglyceride. Typical of this reaction is the reconstitution of 0.33 moles of soybean oil and 0.67 moles of beeswax to produce a new reconstituted oil and a new reconstituted wax.

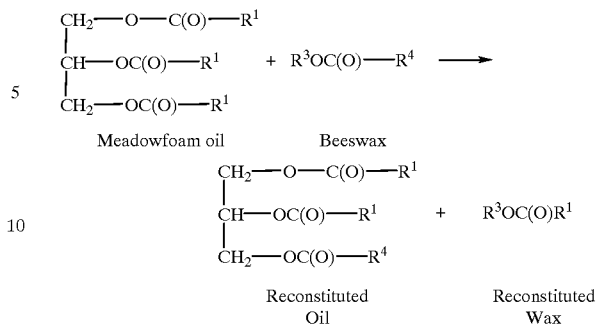

As will become evident from the current disclosure, the reconstituted products prepared using the process of the current invention have altered properties, like melting point, viscosity, pigment dispersion properties and others that make these compounds very useful in a variety of applications, including personal care and preparations of inks, polishes and waxes for industrial applications.

Detailed Description of the Invention

The present invention discloses a process for treating skin using reconstituting triglyceride and waxes which comprises, reacting meadowfoam oil with one or more reactants selected from the group consisting of triglycerides and waxes in the presence of an esterification catalyst at a temperature of between 150 and 250 C. The oils produced by this process have no odor when applied to skin. By modifying the oil by reconstitution the desirable functions of meadowfoam are carried over into other functional oils. For example, A non-odor producing oil based upon soybean oil can be prepared for skin care applications.

In a preferred embodiment, meadowfoam oil is one of the triglycerides reacted. Meadowfoam oil is a unique triglyceride. Meadowfoam Oil has the CAS number 153065-40-8.

These compounds are prepared by reconstituting meadowfoam oil and a triglyceride group consisting of soybean oil, corn oil, sunflower oil, safflower oil, olive oil and cottonseed oil . The process comprises, reacting meadowfoam oil with two or more reactants selected from the group consisting of soybean oil, corn oil, sunflower oil, safflower oil, olive oil and cottonseed oil in the presence of an esterification catalyst at a temperature of between 150 and 250 C.

Preferred Embodiment

The reconstituted triglyceride made by the transesterification reaction of meadowfoam oil and a second triglyceride selected from the group consisting of soybean oil, corn oil, sunflower oil, safflower oil, olive oil and cottonseed oil.

In a preferred embodiment the reconstituted triglyceride of the present invention, said transesterification reaction is conducted by mixing said meadowfoam oil and a second triglyceride selected from the group consisting of soybean oil, corn oil, sunflower oil, safflower oil, olive oil and cottonseed oil then heating said mixture in the presence of an esterification catalyst to a temperature of between 150 and 250° C.

In a preferred embodiment said second triglyceride is soybean oil.

In a preferred embodiment said second triglyceride is castor oil.

In a preferred embodiment said second triglyceride is corn oil.

In a preferred embodiment said second triglyceride is sunflower oil.

In another preferred embodiment said second triglyceride is safflower oil.

In another preferred embodiment said second triglyceride is olive oil.

In another preferred embodiment said second triglyceride is cottonseed oil.

EXAMPLES

Raw Materials

The raw materials useful in the preparation of the products of the current invention are natural products derived from both plant and animal sources. We have described them giving their common name, source CAS numbers and carbon distribution. All these materials are items of commerce, available from many sources including J.W. Hanson Co. Woodbury, N.Y. and Angelia Oils (Kramer Chemical) Glen Rock, N.J.

Triglycerides

Example 1

Milk Fat

Milk fat is the triglyceride from cow's milk, it is also known as butter. It is made up of the following carbon distribution (R value): 4% $C_3H_5$ (butyric), 2% $C_5H_{15}$ (caproic), 2% $C_7H_{15}$ (caprylic), 3% $C_9H_{19}$ (capric), 4% $C_{11}H_{23}$ (lauric), 10% $C_{13}H_{27}$ (myristic), 32% $C_{15}H_{31}$ (palmitic), 14% $C_{17}H_{35}$ (stearic), 30% $C_{17}H_{33}$ (oleic) and 2% $C_{17}H_{31}$ (linoleic). Milk fat has a CAS Number of 144635-07-4, and an EINCS Number: of 415-310-5.

Example 2

Tallow

Tallow is the triglyceride also known as animal fat. It is made up of the following carbon 3% $C_{13}H_{27}$ (myristic), 30% $C_{15}H_{31}$ (palmitic), 20% $C_{17}H_{35}$ (stearic), 40% $C_{17}H_{33}$ (oleic) and 6% $C_{17}H_{31}$ (linoleic). It has a CAS Number of 61789-13-7 and a EINECS Number: 263-035-2.

Example 3

Japan Wax

Japan Wax is a triglyceride secreted by the insect Coccus cerriferus. The wax is deposited over the tree branches in which the insect lives. The wax is scrapped and refined much like beeswax is refined. It is 79% $C_{15}H_{31}$ (palmitic) and has a CAS Number of 8001-139-6

Example 4

Coconut Oil

Coconut oil is the most abundant oil processed. It is the most common oil raw material used in the cosmetic industry. It comes principally from Southeast Asia and the Philippines and is the major source of lauric acid. Coconut oil is 48% $C_{11}H_{23}$ (lauric), and 20% $C_{13}H_{27}$ (myristic). The CAS Number is 8001-31-8.

Example 5

Babassu Oil

Babassu oil is derived from the tallest palm in Brazil (Attelea martiana Martius). Chemically, it is very similar to coconut oil, having a carbon distribution shifted slightly toward the higher molecular weights. It is 45% $C_{11}H_{23}$ (lauric), 17% $C_{13}H_{27}$ (myristic), 8% $C_{15}H_{31}$ (palmitic), and 15% $C_{17}H_{33}$ (oleic). It has a CAS Number of 91078-92-1 and an EINECS Number of 293-376-2.

Example 6

Palm Kernel Oil

Palm kernel oil is a triglyceride derived from the dried fruit of the coconut palm (Cocos nucifera L.). It comes from Southeast Asia. It is 50% $C_{11}H_{23}$ (lauric), 15% $C_{13}H_{27}$ (myristic), and 15% $C_{17}H_{33}$ (oleic) It has a CAS Number of 8023-79-8 and EINECS Number is 232-282-8.

Example 7

Soybean oil

Soybean oil is a triglyceride derived from the soybean (Glycerin max L). The soybean originated in China, as far back as 2,300 BC. It is 30% $C_{17}H_{33}$ (oleic), and 54% $C_{17}H_{31}$ (linoleic). The CAS Number is 8001-22-7 and the EINECS Number is 232-274-4.

Example 8

Peanut Oil

Peanut oil is a triglyceride derived from peanuts (Arachis hypogea L.). It is cultivated in many areas of the world, since it is easy to grow. It is 60% $C_{17}H_{33}$ (oleic), and 23% $C_{17}H_{31}$ (linoleic). It has a CAS Number of 8002-03-07 and a EINECS Number of 232-296-4.h Example 9

Corn Oil

Corn oil is a triglyceride derived from corn (Zea mais, Graminae). It is cultivated in all the temperate areas of the world. It is 46% $C_{17}H_{33}$ (oleic) and 43% $C_{17}H_{31}$ (linoleic). The CAS Number is 8001-30-7.

Example 10

Sunflower Seed Oil

Sunflower seed oil is a triglyceride derived from the seeds of the sunflower (Helianthus annus L.). It was originally cultivated in North America by native Indians. It is now cultivated in North America, Russia, Europe South America, India and China. It is a rather common plant. It is 20% $C_{17}H_{33}$ (oleic ) and 70% $C_{17}H_{31}$ (linoleic). The EINECS Number is 232-273-9 and the CAS Number is 8001-21-6.

Example 11

Grapeseed Oil

Grapeseed oil is a triglyceride derived from grape (Vitis Vinifera). It is cultivated in many areas of the world, but originated in the Mediterranean coast (Italy, France, Turkey, Greece and Yugoslavia). It is 70% $C_{17}H_{29}$ (linoleic). EINECS number is 287-896-9 and the CAS Number is 8024-22-4.

Example 12

Safflower Oil

Safflower oil is a triglyceride derived from the species Carthamus Tinctorius. This is the high oleic species. It originates in the Orient, but the U.S. production has been selected to maximize oil content. The oil is 77% $C_{17}H_{33}$ (oleic), and 17% $C_{17}H_{31}$ (linoleic). The CAS Number is 8001-23-9, and the EINECS Number is 232-276-6.

Example 13

Poppy Seed Oil

Poppy seed oil is a triglyceride derived from the poppy (Papaver orientiale). It was originally cultivated in Asia Minor, but is now produced in Europe. It is 10% $C_{15}H_{31}$ (palmitic), 15% C17H33 (oleic), and 73%, C17H31 (linoleic). The CAS Number is 8002-11-7.

Example 14

Sweet Almond Oil

Sweet almond oil is a triglyceride derived from the almond (Prunus amygdalus). It is cultivated in all the temperate areas of the world. The oil is 73% C17H33 (oleic), and 20% C17H31 (linoleic). The CAS Number is 8007-69-0

Example 15

Hazelnut Oil

Hazelnut oil is a triglyceride derived from the nut of the hazelnut tree (Corylus avellana). It is cultivated in Europe, principally Italy, Spain and Turkey. Hazelnut oil contains natural preservatives and antioxidants, which render the oil very stable. It is 80% C17H33 (oleic) and 15% C17H31 (linoleic)

Example 16

Walnut Oil

Walnut oil is a triglyceride derived from the walnut (Juglans regia). It originated in Persia, and is now cultivated in Europe. Southern France is the major area in which Walnuts are grown. It is 26% C17H33 (OLEIC), 48% C17H31 (linoleic), and 16% C17H29 (linolenic). The CAS Number is 8024-09-7, and the EINECS Number is 84604-00-2.

Example 17

Olive Oil

Olive oil is a triglyceride, which has occupied a unique position in civilization. It is the oldest oil known to man. It is produced throughout the area that was once the Roman Empire. Olive oil is 84% C17H33 (oleic). The CAS Number is 8001-25-0, and the EINECS Number is 232-277-0.

Example 18

Avocado Oil

Avocado oil is a triglyceride coming from the avocado (Persea grantissima). The pulp of the fruit has a great deal of oil present (70% by weight). It is 22% C15H31 (palmitic), 62% C17H33 (oleic), and 13% C17H31 (linoleic). The CAS Number is 8024-32-6, and the EINECS Number is 232-274-4.

Example 19

Sesame Oil

Sesame oil is a triglyceride, which is derived from Sesamun indicum. It is cultivated in Africa, Europe, China, Central and South America and the southern U.S. It is one of the world's oldest crops. It is 47% C17H33 (oleic), and 40% C17H31 (linoleic). The CAS Number is 8008-74-0, and the EINECS Number is 232-370-6.

Example 20

Cottonseed Oil

Cottonseed oil is a triglyceride derived from cotton (Gossypium hirsutum). Cotton, like soybean, is a very important crop, in that the crop has a protein, and fatty component, but unlike soybean, the fiber is very useful in textile applications. It is 21% C15H31 (palmitic), 32% C17H33 (oleic), and 44% C17H31 (linoleic). The CAS Number is 8001-29-4 and the EINECS Number is 232-280-7

Example 21

Palm Oil

Palm oil is a triglyceride extracted from the fruit of Elaeis guineensis Jacq, which is among the most efficient oil producing plants per acre in the world. It is 42% C15H31 (palmitic), and 44% C17H33 (oleic). The CAS Number is 8002-75-3, and the EINECS Number is 232-316-1

Example 22

Rice Bran Oil

Rice Bran oil is a triglyceride extracted from rice. It comes from Japan. It is 18% C15H31 (palmitic), 41% C17H33 (oleic), and 37% C17H31 (linoleic). The CAS Number is 68553-81-1 and the EINECS Number is 271-397-8.

Example 23

Canola

Canola oil is a triglyceride produced from genetically modified rapeseed. It is 77% C17H33 (oleic), 11% C17H31 (linoleic). The CAS Number is 8002-13-9.

Example 24

Cocoa Butter

Coca butter is a triglyceride obtained from the cocoa bean (Theobroma Cacoa L.). The species was originally found along the Amazon. It is now grown commonly along the equator where there is abundant rainfall. Cocoa Butter is the ingredient that gives chocolate its characteristic melting properties and unique texture. "Pure prime pressed" denotes the highest possible quality of cocoa butter used in the food industry. It is 27% C15H31 (palmitic), 35% C17H35 (stearic), and 35% C17H33 (oleic). The CAS Number is 8002-31-1

Example 25

Borneo Illipe (Shea Butter)

Borneo Illipe is a triglyceride derived from the tree (Shorea stenoptera L.), which is native to India. It is also called Shea Butter. It is 20% C15H31 (palmitic), 45% C17H35 (stearic), and 33% C17H33 (oleic). The CAS Number is 977026-99-5, and the EINECS Number is 293-515-7.

Example 26

Linseed Oil

Linseed oil is a triglyceride derived from flax (Linum usitatissium). It is cultivated in all the temperate areas of the world. Linseed oil is a drying oil, meaning it dries into a solid. This is due to the high number of double bonded and the triple bonded species present in the material. Linseed oil is a drying oil. Linseed oil is 17%, C17H 33 (oleic), 15% C17H31 (linoleic), and 61% C18H29 (linolenic). The CAS Number is 8001-26-1, and the EINECS Number is 232-278-6.

Example 27

Veronia Oil

Veronia oil is a triglyceride, which is obtained from the seed of Veronia galamensis. It contains a very high concentration of epoxy functionality, making it unique. It is 79% C17H31O (Cis 12–13 epoxy oleic). The CAS Number is 169360-96.

Example 28

Tung Oil

Tung oil is a triglyceride obtained from the seed of the Tung tree (Aleurites fordii). The tree is native to China and Indochina. Tung is described as a drying oil. This is because the abundance of double and triple bonds in it, particularly the high concentration of the conjugated double bonds, make this oil homo polymerize into a film. Tung oil is 80% C17H29 (conj. double bonds). The CAS Number is 8001-20-5

Example 29

Ongokea Oil

Ongokea oil is a triglyceride derived from the species Ongokea gore. It originates in Africa. This material is somewhat unique because of it's high concentration of an acetylenic bond. Ongokea oil is a drying oil. It is 80% C17H29 having a unique triple bond.

Waxes

Example 30

Beeswax

Beeswax is a complex ester, produced by worker bees, Apis mellifica. Beeswax, which is also known as white wax, is an insect wax cultured worldwide; it is found on all continents of the globe. The chemical composition of the wax depends on the species of the bee producing the wax. To extract the beeswax for use, the honeycomb is melted or boiled with water and the crude wax is skimmed off the top. The color of the crude material is dependent upon the type of flower producing the pollen and the age of the hive. Beeswax is a complex structure and as such, possesses unique properties that renders it an invaluable raw material for many of today's industries. Beeswax was the first wax. It consists of about 15% free fatty acids, 15% hydrocarbon resins, and the balance the esters.

Carbon Distribution

Principal Ester Composition

| Alcohol/Acid | % |
|---|---|
| C-30/C-16 | 23 |
| C-30/C-26 | 12 |
| C-30/C-30 | 12 |
| C-26/C-16* | 10 |

*Hydroxy-palmitate

The CAS Number is 8006-40-4, the EINECS Number is 232-383-7.

Example 31

Carnuba Wax

At present, the only place in the world where the Carnauba Palm tree can be found is in northeastern Brazil. This Palm tree (Capernicea cerifera), often called the "tree of life," produces a wax on its leaves, protecting them from the severe weather conditions of the area. Harvesting occurs around September following traditional procedures, the leaves are cut and are laid on the ground to dry in the sun. Modern technology takes over to scrape this valued product from its leaf.

Carnuba wax is composed of mono and di hydroxy containing fatty alcohols, having 28 to 34 carbon atoms, and hydroxy acids, their esters and polyesters. This polymeric nature of the wax results in its hardness and high melting point. The CAS Number is 8015-86-9.

Example 32

Jojoba Oil

Jojoba is an ester derived from the woody evergreen shrub Simmondsia chinensis (link). Jojoba is a desert shrub that grows in coarse well-drained desert soil. It is found in southern Arizona and northwest Mexico.

Jojoba oil is a liquid ester having C20 to C22 acids and alcohols. It has a CAS Number of 61789-91-1

Example 33

Candellia Wax

Candellia Wax is extracted from the outer surface of Candellia plants, which are native to the arid regions of Northern Mexico, The plants grow wild in the plains and in the foothills of Mexico's North-Central plateau. With a Melting point ranging from 66 to 71 C., Candellia is well suited to the preparation of many wax products where resistance to heat is an important consideration. Candelilla wax is used in polish dressings, coatings, and finishes, where a reasonably high melting point is desirable. In addition, this wax blends easily with fatty acids, paraffin, and other waxes used in the manufacture of candles and tapers. Candellia can be used for dyes in the printing of various materials providing excellent lubricant properties and resistance to high pressure. Candellia Wax is composed of hydrocarbon (50%) and the remainder is fatty acids, aliphatic triterpenic alcohols and their esters as well as some resin.

| Component | % Weight | Chemical Nature |
|---|---|---|
| Acids | 8 | C30–C34 |
| Alcohols | 10 | C20–C32 |
| Esters | 30 | C42–C64 |
| Hydrocarbons | 50 | C31 |
| Resin | 2 | — |

CAS Number: 8006-44-8

Raw Material Examples

| Example (Number) | Description | Example (Number) | Description |
|---|---|---|---|
| Raw Material Examples | | | |
| (1) | milk fat, | (2) | tallow, |
| (3) | Japan wax, | (4) | coconut oil, |
| (5) | babassu oil, | (6) | palm kernel oil, |
| (7) | soybean oil, | (8) | peanut oil, |
| (9) | corn oil, | (10) | sunflower oil, |
| (11) | grapeseed oil, | (12) | safflower oil, |
| (13) | poppy seed oil, | (14) | sweet almond oil, |
| (15) | hazelnut oil, | (16) | walnut oil, |
| (17) | olive oil, | (18) | avacado oil, |
| (19) | sesame oil, | (20) | cottonseed oil, |
| (21) | palm oil, | (22) | rice bran oil, |
| (23) | canola oil, | (24) | coco butter oil, |
| (25) | shea butter, | (26) | linseed |
| (27) | veronia oil, | (28) | Tung |
| (29) | ongokea oil, | | |
| Raw Material Waxes | | | |
| (30) | beeswax, | | |

-continued

| Example (Number) | Description | Example (Number) | Description |
|---|---|---|---|
| (31) | carnauba wax, | | |
| (32) | jojoba oil, | | |
| (33) | candellia wax. | | |

General Procedure

1. Reconstitution reacting two or more different triglycerides.

The compounds of the present invention are prepared according to the following procedure:

Into a suitable vessel with agitation and nitrogen sparge is placed the specified number of grams of the first specified triglyceride. Next add the specified number of grams of the specified second triglyceride. A suitable esterification catalyst is then added. Esterification catalysts are selected from the group consisting of methane sulfonic acid, sulfuric acid, oragno-tin compounds, titinates. Of particular interest is the use of stannous oxylate. Stannous oxylate is used at a concentration of 0.1 percent based upon the total number of grams of all materials charged. The contents of the vessel are heated to between 150–250 C. A preferred range is 180–190 C. The contents are held at this temperature for at least four hours. During that time the batch clears and becomes homogenous and the reaction progress is followed by thin layer chromatography. The concentration of the original triglycerides drop down to low levels and the new reconstituted triglycerides are formed. The materials are cooled and used without additional purification. Clay treatment to improve color or filtration may be used if desired.

Example 34

Into a suitable vessel with agitation and nitrogen sparge is placed 100.0 grams of the first specified triglyceride (Example 1). Next add 500.0 grams of the second triglyceride (Example 2). Next add 0.1% stannous oxylate. Stannous oxylate is used at a concentration of 0.1 percent based upon the total number of grams of all materials charged. The contents of the vessel are heated to between 180–190 C. for at least six hours. During that time the batch clears and becomes homogenous and the reaction progress is followed by thin layer chromatography. The concentration of the original concentration of the triglycerides drop down to low levels and the new reconstituted triglycerides are formed.

Example 35–69

Example 34 is repeated, only this time the specified number of grams of the specified first triglyceride are substituted for the original first triglyceride and the specified number of grams of the specified second triglyceride is substituted for the original second triglyceride.

| | First Triglyceride | | Second Triglyceride | |
|---|---|---|---|---|
| Example | Example | Grams | Example | Grams |
| 35 | 1 | 500.0 | 30 | 500.0 |
| 36 | 2 | 500.0 | 29 | 500.0 |
| 37 | 3 | 500.0 | 30 | 400.0 |
| 38 | 4 | 500.0 | 29 | 400.0 |
| 39 | 5 | 500.0 | 28 | 300.0 |
| 40 | 6 | 500.0 | 27 | 300.0 |
| 41 | 7 | 500.0 | 26 | 600.0 |
| 42 | 8 | 500.0 | 25 | 100.0 |
| 43 | 9 | 500.0 | 24 | 50.0 |
| 44 | 10 | 500.0 | 23 | 50.0 |
| 45 | 11 | 500.0 | 22 | 150.0 |
| 46 | 12 | 500.0 | 21 | 250.0 |
| 47 | 13 | 500.0 | 20 | 500.0 |
| 48 | 14 | 500.0 | 19 | 5.0 |
| 49 | 15 | 500.0 | 18 | 150.0 |
| 50 | 16 | 500.0 | 17 | 500.0 |
| 51 | 17 | 500.0 | 16 | 325.0 |
| 52 | 18 | 500.0 | 15 | 450.9 |
| 53 | 19 | 500.0 | 14 | 500.0 |
| 54 | 20 | 500.0 | 13 | 5.0 |
| 55 | 21 | 500.0 | 12 | 900.0 |
| 56 | 22 | 500.0 | 11 | 500.0 |
| 57 | 23 | 500.0 | 10 | 500.0 |
| 58 | 24 | 500.0 | 9 | 50.0 |
| 59 | 25 | 500.0 | 8 | 400.0 |
| 60 | 26 | 500.0 | 7 | 400.0 |
| 61 | 27 | 500.0 | 6 | 300.0 |
| 62 | 28 | 500.0 | 5 | 35.0 |
| 63 | 29 | 500.0 | 4 | 500.0 |
| 64 | 30 | 500.0 | 3 | 500.0 |
| 65 | 26 | 500.0 | 2 | 150.0 |
| 66 | 28 | 500.0 | 1 | 50.0 |
| 67 | 21 | 500.0 | 1 | 100.0 |
| 68 | 21 | 500.0 | 2 | 500.0 |
| 69 | 23 | 500.0 | 3 | 250.0 |

Example 70

Into a suitable vessel with agitation and nitrogen sparge is placed 100.0 grams of the first specified triglyceride (Example 1), and 100 grams of specified second triglyceride (Example 2). Next add 500.0 grams of the third triglyceride (Example 3). Next add 0.1% stannous oxylate. Stannous oxylate is used at a concentration of 0.1 percent based upon the total number of grams of all materials charged. The contents of the vessel are heated to between 180–190 C. for at least six hours. During that time the batch clears and becomes homogenous and the reaction progress is followed by thin layer chromatography. The concentration of the original triglycerides drop down to low levels and the new reconstituted triglycerides are formed.

Example 71–79

Example 70 is repeated, only this time the specified number of grams of the specified first triglyceride are substituted for the original first triglyceride, the specified number of grams of the specified second triglyceride is substituted for the original second triglyceride and the specified number of grams of the specified third triglyceride is substituted for the original third triglyceride.

| | First Triglyceride | | Second Triglyceride | | Third Triglyceride | |
|---|---|---|---|---|---|---|
| Example | Example | Grams | Example | Grams | Example | Grams |
| 72 | 1 | 500.0 | 29 | 100.0 | 16 | 100.0 |
| 73 | 2 | 500.0 | 28 | 200.0 | 17 | 200.0 |

-continued

| Exam-ple | First Triglyceride Example | Grams | Second Triglyceride Example | Grams | Third Triglyceride Example | Grams |
|---|---|---|---|---|---|---|
| 74 | 3 | 500.0 | 27 | 500.0 | 18 | 50.0 |
| 75 | 4 | 500.0 | 26 | 400.0 | 20 | 5.0 |
| 76 | 5 | 500.0 | 25 | 200.0 | 21 | 150.0 |
| 77 | 6 | 500.0 | 28 | 50.0 | 23 | 200.0 |
| 78 | 7 | 500.0 | 26 | 5.0 | 25 | 100.0 |
| 79 | 8 | 500.0 | 29 | 5.0 | 28 | 50.0 |

2. Reconstitution reacting two or more different waxes.

The compounds of the present invention are prepared according to the following procedure:

Into a suitable vessel with agitation and nitrogen sparge is placed the specified number of grams of the first specified wax. Next add the specified number of grams of the specified second wax. A suitable esterification catalyst is then added. Esterification catalysts are selected from the group consisting of methane sulfonic acid, sulfuric acid, oragno-tin compounds, titinates. Of particular interest is the use of stannous oxylate. Stannous oxylate is used at a concentration of 0.1 percent based upon the total number of grams of all materials charged. The contents of the vessel are heated to between 150–250 C. A preferred range is 180–190 C. The contents are held at this temperature for at least four hours. During that time the batch clears and becomes homogenous and the reaction progress is followed by thin layer chromatography. The concentration of the original wax drop down to low levels and the new reconstituted waxes are formed. The materials are cooled and used without additional purification. Clay treatment to improve color or filtration may be used if desired.

Example 80

Into a suitable vessel with agitation and nitrogen sparge is placed 500.0 grams of the first specified wax (Example 30). Next add 500.0 grams of the second wax (Example 31). Next add 0.1% stannous oxylate. Stannous oxylate is used at a concentration of 0.1 percent based upon the total number of grams of all materials charged. The contents of the vessel are heated to between 180–190 C. for at least six hours. During that time the batch clears and becomes homogenous and the reaction progress is followed by thin layer chromatography. The concentration of the original wax drop down to low levels and the new reconstituted waxes are formed.

Example 81–91

Example 80 is repeated, only this time the specified number of grams of the specified first wax are substituted for the original first wax and the specified number of grams of the specified second wax is substituted for the original second wax.

| Example | First Wax Example | Grams | Second Wax Example | Grams |
|---|---|---|---|---|
| 81 | 31 | 500.0 | 30 | 500.0 |
| 83 | 32 | 500.0 | 31 | 500.0 |
| 84 | 33 | 500.0 | 32 | 500.0 |
| 85 | 30 | 500.0 | 33 | 500.0 |
| 86 | 31 | 500.0 | 33 | 500.0 |
| 87 | 32 | 500.0 | 30 | 100.0 |
| 88 | 33 | 500.0 | 31 | 300.0 |

Example 89

Into a suitable vessel with agitation and nitrogen sparge is placed 100.0 grams of the first specified wax (Example 30), and 100 grams of second specified wax (Example 31). Next add 500.0 grams of the third wax (Example 32). Next add 0.1% stannous oxylate. Stannous oxylate is used at a concentration of 0.1 percent based upon the total number of grams of all materials charged. The contents of the vessel are heated to between 180–190 C. for at least six hours. During that time the batch clears and becomes homogenous and the reaction progress is followed by thin layer chromatography. The concentration of the original triglycerides drop down to low levels and the new reconstituted triglycerides are formed.

Example 90–102

Example 89 is repeated, only this time the specified number of grams of the specified first wax is substituted for the original first triglyceride, the specified number of grams of the specified second wax is substituted for the original second wax and the specified number of grams of the specified third wax is substituted for the original third wax.

| Exam-ple | First Wax Example | Grams | Second Wax Example | Grams | Third Wax Example | Grams |
|---|---|---|---|---|---|---|
| 90 | 30 | 500.0 | 33 | 250.0 | 32 | 55.0 |
| 91 | 31 | 500.0 | 32 | 250.0 | 30 | 127.0 |
| 92 | 32 | 500.0 | 31 | 250.0 | 33 | 485.0 |
| 93 | 33 | 500.0 | 30 | 250.0 | 31 | 560.0 |
| 94 | 30 | 500.0 | 31 | 250.0 | 31 | 100.5 |
| 95 | 31 | 500.0 | 32 | 250.0 | 32 | 158.0 |
| 96 | 32 | 500.0 | 33 | 250.0 | 33 | 135.0 |
| 97 | 33 | 500.0 | 32 | 250.0 | 31 | 159.0 |
| 98 | 30 | 500.0 | 31 | 250.0 | 33 | 600.0 |
| 99 | 31 | 500.0 | 30 | 250.0 | 33 | 152.0 |
| 100 | 32 | 500.0 | 31 | 25.0 | 33 | 50.0 |
| 101 | 33 | 500.0 | 31 | 10.0 | 33 | 5.0 |
| 102 | 30 | 500.0 | 31 | 5.0 | 33 | 5.0 |

3. Reconstitution reacting one or more waxes and one or more triglycerides.

The compounds of the present invention are prepared according to the following procedure:

Into a suitable vessel with agitation and nitrogen sparge is placed the specified number of grams of the specified triglyceride. Next add the specified number of grams of the specified wax. A suitable esterification catalyst is then added. Esterification catalysts are selected from the group consisting of methane sulfonic acid, sulfuric acid, oragno-tin compounds, titinates. Of particular interest is the use of stannous oxylate. Stannous oxylate is used at a concentration of 0.1 percent based upon the total number of grams of all materials charged. The contents of the vessel are heated to between 150–250 C. A preferred range is 180–190 C. The contents are held at this temperature for at least four hours. During that time the batch clears and becomes homogenous and the reaction progress is followed by thin layer chromotography. The concentration of the original reactants drop down to low levels and the new reconstituted products are formed. The materials are cooled and used without additional purification. Clay treatment to improve color or filtration may be used if desired.

Example 103

Into a suitable vessel with agitation and nitrogen sparge is placed 500.0 grams of the specified triglyceride (Example 1). Next add 500.0 grams of the wax (Example 30). Next add 0.1% stannous oxylate. Stannous oxylate is used at a concentration of 0.1 percent based upon the total number of grams of all materials charged. The contents of the vessel are heated to between 180–190 C. for at least six hours. During that time the batch clears and becomes homogenous and the reaction progress is followed by thin layer chromatography. The concentration of the original reactants drop down to low levels and the new reconstituted products are formed.

Example 104–130

Into a suitable vessel with agitation and nitrogen sparge is placed 500.0 grams of the triglyceride (Example 1). Next add 500.0 grams of the wax (Example 30). Next add 0.1% stannous oxylate. Stannous oxylate is used at a concentration of 0.1 percent based upon the total number of grams of all materials charged. The contents of the vessel are heated to between 180–190 C. for at least six hours. During that time the batch clears and becomes homogenous and the reaction progress is followed by thin layer chromatography. The concentration of the original reactants drop down to low levels and the new reconstituted products are formed.

| | Triglyceride | | Wax | |
|---|---|---|---|---|
| Example | Example | Grams | Example | Grams |
| 104 | 7 | 95.0 | 30 | 5.0 |
| 105 | 7 | 90.0 | 30 | 10.0 |
| 106 | 7 | 30.0 | 30 | 70.0 |
| 107 | 7 | 20.0 | 30 | 80.0 |
| 108 | 29 | 95.0 | 30 | 5.0 |
| 109 | 29 | 90.0 | 30 | 10.0 |
| 110 | 29 | 80.0 | 30 | 20.0 |
| 111 | 29 | 30.0 | 30 | 70.0 |
| 112 | 29 | 20.0 | 30 | 80.0 |
| 113 | 1 | 500.0 | 31 | 500.0 |
| 114 | 2 | 500.0 | 31 | 500.0 |
| 115 | 3 | 500.0 | 31 | 500.0 |
| 116 | 4 | 500.0 | 31 | 50.0 |
| 117 | 5 | 500.0 | 31 | 10.0 |
| 118 | 6 | 500.0 | 31 | 500.0 |
| 119 | 7 | 500.0 | 31 | 500.0 |
| 120 | 8 | 500.0 | 31 | 500.0 |
| 121 | 9 | 500.0 | 31 | 500.0 |
| 122 | 10 | 500.0 | 31 | 500.0 |
| 123 | 11 | 500.0 | 31 | 50.0 |
| 124 | 12 | 500.0 | 31 | 500.0 |
| 125 | 13 | 500.0 | 31 | 500.0 |
| 126 | 14 | 500.0 | 32 | 500.0 |
| 127 | 15 | 500.0 | 32 | 500.0 |
| 128 | 16 | 500.0 | 32 | 500.0 |
| 129 | 17 | 500.0 | 32 | 500.0 |
| 130 | 18 | 500.0 | 33 | 500.0 |

Example 131

Into a suitable vessel with agitation and nitrogen sparge is placed 500.0 grams of the specified triglyceride (Example 1). Next add 500.0 grams of the wax (Example 34). Next, add 500.0 grams of the second triglyceride (Example 2). Next add 0.1% stannous oxylate. Stannous oxylate is used at a concentration of 0.1 percent based upon the total number of grams of all materials charged. The contents of the vessel are heated to between 180–190 C. for at least six hours. During that time the batch clears and becomes homogenous and the reaction progress is followed by thin layer chromatography. The concentration of the original reactants drop down to low levels and the new reconstituted products are formed.

Example 132–150

Repeat example 131 only this time replace the specified amount of the first triglyceride with the specified amount of the new specified triglyceride. Replace the specified amount of wax with the specified amount of the specified wax, and the specified amount of the specified second triglyceride with the specified amount of the newly specified second triglyceride

| Exam- | Triglyceride 1 | | Wax | | Triglyceride 2 | |
|---|---|---|---|---|---|---|
| ple | Example | Grams | Example | Grams | Example | Grams |
| 138 | 19 | 500.0 | 30 | 500.0 | 1 | 50.0 |
| 139 | 20 | 500.0 | 31 | 500.0 | 2 | 500.0 |
| 140 | 21 | 500.0 | 32 | 50.0 | 3 | 5.0 |
| 141 | 22 | 600.0 | 33 | 400.0 | 4 | 500.0 |
| 142 | 23 | 600.0 | 30 | 10.0 | 5 | 500.0 |
| 143 | 24 | 600.0 | 31 | 5.0 | 6 | 500.0 |
| 144 | 25 | 600.0 | 32 | 500.0 | 7 | 500.0 |
| 145 | 26 | 600.0 | 33 | 500.0 | 8 | 500.0 |
| 146 | 27 | 600.0 | 30 | 500.0 | 9 | 50.0 |
| 147 | 28 | 500.0 | 31 | 500.0 | 10 | 5.0 |
| 148 | 29 | 500.0 | 32 | 500.0 | 11 | 500.0 |
| 149 | 1 | 500.0 | 33 | 500.0 | 12 | 500.0 |
| 150 | 2 | 400.0 | 33 | 45.0 | 7 | 500.0 |

What is claimed:

1. A process for treating skin which comprises contacting the skin with an effective moisturizing concentration of a reconstituted triglyceride made by the transesterification reaction of meadowfoam oil and a second triglyceride selected from the group consisting of soybean oil, corn oil, sunflower oil, safflower oil, olive oil and cottonseed oil.

2. A process of claim 1, wherein said transesterification reaction is conducted by mixing said meadowfoam oil and a second triglyceride selected from the group consisting of soybean oil, corn oil, sunflower oil, safflower oil, olive oil and cottonseed oil then heating said mixture in the presence of an esterification catalyst to a temperature of between 150 and 250 C.

3. A process of claim 2 wherein said second triglyceride is soybean oil.

4. A process of claim 2 wherein said second triglyceride is corn oil.

5. A process of claim 2 wherein said second triglyceride is sunflower oil.

6. A process of claim 2 wherein said second triglyceride is safflower oil.

7. A process of claim 2 wherein said second triglyceride is olive oil.

8. A process of claim 2 wherein said second triglyceride is cottonseed oil.

9. A process of claim 2 wherein said second triglyceride is soybean oil.

10. A process of claim 2 wherein said second triglyceride is corn oil.

11. A process of claim 2 wherein said second triglyceride is sunflower oil.

12. A process of claim 2 wherein said second triglyceride is safflower oil.

13. A process of claim 2 wherein said second triglyceride is olive oil.

14. A process of claim 2 wherein said second triglyceride is cottonseed oil.

* * * * *